United States Patent [19]

Antholz et al.

[11] 4,221,684
[45] Sep. 9, 1980

[54] ABSORBENT POLYMERIC COMPOSITIONS DERIVED FROM CORN FLOUR AND STARCH

[75] Inventors: Phillip Antholz; E. Jack Swarthout, both of Paris, Ill.

[73] Assignee: Illinois Cereal Mills, Paris, Ill.

[21] Appl. No.: 970,313

[22] Filed: Dec. 18, 1978

[51] Int. Cl.$^2$ ............................................... C08L 3/02
[52] U.S. Cl. ..................... 260/17.4 GC; 47/DIG. 10; 128/284; 128/285; 128/290 R
[58] Field of Search ............................... 260/17.4 GC

[56] References Cited

U.S. PATENT DOCUMENTS

| | | | |
|---|---|---|---|
| 3,425,971 | 2/1969 | Gugliemelli et al. | 260/17.4 GC |
| 3,661,815 | 5/1972 | Smith | 260/17.4 GC |
| 4,069,177 | 1/1978 | Smith | 260/17.4 GC |
| 4,076,663 | 2/1978 | Masuda et al. | 260/17.4 GC |
| 4,134,863 | 1/1979 | Fanta et al. | 260/17.4 GC |

Primary Examiner—Edward M. Woodberry
Attorney, Agent, or Firm—Burns, Doane, Swecker & Mathis

[57] ABSTRACT

Absorbent polymeric compositions are disclosed which are prepared by graft copolymerizing acrylonitrile onto a starch or corn flour-containing substrate followed by subjecting the graft copolymer to alkaline saponification. A polymeric composition of increased absorbency is obtained by isolating the saponified graft copolymer from solution as a colloidal precipitate subsequent to the slow addition of an alcohol to the solution.

10 Claims, No Drawings

ABSORBENT POLYMERIC COMPOSITIONS DERIVED FROM CORN FLOUR AND STARCH

BACKGROUND OF THE INVENTION

Processes for polymerizing acrylonitrile with starch are well known in the art. For example, such processes are shown in U.S. Pat. Nos. 2,922,768; 3,201,366; 3,661,815; 3,669,915; 3,935,099; 3,985,616; 3,997,484; 4,005,040; 4,045,387; and 4,069,177.

Most of these processes make use of starch (e.g., pearl starch) to produce a graft copolymer which forms a highly water absorbent polymeric composition. These starch-containing polymers can absorb water in amounts of 1,000 times or more by weight of water per weight of the polymeric composition. These products are highly useful in many applications including such uses as incorporation in disposable diapers, surgical pads and sheets, paper towels, disposable paper pads and the like.

The above-mentioned U.S. Pat. No. 4,045,387 discloses a process for producing a highly absorbent polymeric composition which is derived from flour such as corn or wheat flour. The process disclosed therein is purported to produce a product which will absorb from 1,800 to 3,000 times its weight of deionized water. It has been found that when corn flour or starch is used in the process of this patent to produce a polymeric composition, the polymeric composition will form a highly absorbent product consisting of discrete gel particles when contacted with such large amounts of water. That is, the polymeric composition consists of highly swollen gel particles which still maintain definite structural boundaries corresponding somewhat to the shape of the original particle prior to hydration.

Polymeric compositions which can absorb water in amounts of 5,000 to 10,000 times their weight of deionized water in the form of a soft gel in the absence of discrete particles would be highly desirable in certain applications, such as, for example as thickening and viscosity control agents for aqueous systems, and soil porosity control agents. It has been found impossible, however, to produce a soft gel from starch or corn flour utilizing the process of U.S. Pat. No. 4,045,387 which will absorb such large amounts of water. Similarly, it has also been found impossible to produce a soft gel from starch or corn flour utilizing the process of U.S. Pat. No. 3,997,484 which will absorb such large amounts of water.

OBJECTS AND SUMMARY OF THE INVENTION

It is an object of this invention to provide a process for forming a polymeric composition which will absorb large amounts of water in a soft gel form.

It is also an object of this invention to provide a process for the formation of a polymeric composition from corn flour or starch which will absorb large amounts of water is a soft gel form.

It is further an object of this invention to provide a polymeric composition which will absorb large amounts of water in a soft gel form.

It is still further an object of this invention to obviate or substantially eliminate the disadvantages of the prior art as outlined above.

In one aspect of the present invention there is provided a process for forming a water-insoluble, aqueous fluid-absorbing graft copolymer composition comprising:

(a) graft copolymerizing acrylonitrile onto a cornflour or starch containing substrate to form a graft copolymer;

(b) saponifying the graft copolymer in an aqueous solution to form a water-soluble saponified graft copolymer;

(c) slowly adding an alcohol to said saponified graft copolymer-containing aqueous solution to form a colloidal precipitate of said saponified graft copolymer;

(d) ceasing the slow addition of said alcohol to said aqueous solution upon formation of said colloidal precipitate; and (e) recovering and drying said saponified graft copolymer with minimal exposure to moisture to form a water-insoluble, aqueous fluid-absorbing copolymer composition.

In another aspect of the present invention there are provided aqueous fluid-absorbing compositions produced by the process of the present invention and comprising water-insoluble, alkali salts of saponified graft copolymers of acrylonitrile and a starch or corn flour-containing substrate, said graft copolymers being water-insoluble solids capable of absorbing above about 3000 and up to about 10,000 parts of water by weight per part of said water-insoluble solids while remaining substantially as a soft gel.

DETAILED DESCRIPTION OF THE INVENTION

It has been found that the recovery of saponified acrylonitrile-corn flour or starch copolymers from solution as a colloidal precipitate utilizing slow alcohol addition results in the ultimate formation of a water-insoluble, aqueous fluid-absorbing polymeric composition of increased absorbency which sets up as a soft gel.

As noted above, corn flour or starch processed according to known processes, i.e., the process of U.S. Pat. No. 4,045,387, produces a gel which purportedly absorbs up to 3,000 times its weight in deionized water. As also noted above, starch processed according to known processes, i.e., the process of U.S. Pat. No. 3,997,484, produces a gel which purportedly absorbs up to 1500 times its weight in deionized water. By contrast, water soluble starch or corn flour-containing copolymers produced by the graft polymerization-saponification processes disclosed in U.S. Pat. Nos. 4,045,387 or 3,997,484 and recovered in the water-insoluble form from solution by slow alcohol addition in accordance with the process of this invention produce soft gels which can absorb up to 10,000 times their weight of deionized water.

The use of alcohol precipitation as an isolation technique in the recovery of saponified polyacrylonitrile-containing starch graft copolymers from solution is known per se as evidenced by the disclosure of U.S. Pat. Nos. 4,045,387 and 3,425,971. However, the slow addition of an alcohol in order to form a colloidal precipitate of the copolymer and the subsequent removal of water from the copolymer precipitate with minimal exposure to moisture are not disclosed therein.

The corn flour which may be utilized in the present invention is milled from corn and typically contains about 85 percent starch and 10 percent protein, the remainder being made up of fat, fiber and ash.

Any starch-containing flour may be employed as a substrate in the instant invention. Preferred flours contain in excess of 75% starch, with the cereal grain flours particularly preferred. Exemplary substrates include whole ground corn meal, wheat flour, and rice starch.

The corn flour or starch in dry form is mixed with an aqueous solution to form a starch or corn flour-containing substrate and the substrate preferably is then gelatinized. The gelatinization, graft polymerization and saponification steps are performed in accordance with the process of U.S. Pat. No. 4,045,387, the disclosure of which is hereby incorporated herein by reference.

The starch or corn flour-containing substrate is gelatinized by heating the mixture to an elevated temperature which is typically about 70° C. or higher, i.e., at a temperature of from about 80° to 100° C. in order to obtain a smooth, viscous gelatinized dispersion. Gelatinization may be conducted under an inert gas atmosphere, i.e., by bubbling a slow stream of nitrogen through the dispersion.

After gelatinization, the substrate is cooled and a polyacrylonitrile-containing starch graft copolymer is then formed by contacting the starch or corn flour-containing substrate with acrylonitrile in the presence of a suitable polymerization catalyst. The mixture is allowed to stand for a suitable period of time, e.g., 2 to 3 hours or more, to form the graft copolymer. Generally, the graft copolymers have a weight ratio of starch or corn flour to polyacrylonitrile of from about 3:1 to about 1:3, preferably from about 1.5:1 to about 1:1.5.

The graft copolymer is then saponified with an alkali metal hydroxide, preferably sodium hydroxide or potassium hydroxide. Again, saponification may be performed in accordance with the teachings of U.S. Pat. No. 4,045,387. Generally, however, the graft copolymer is saponified with an alkali metal hydroxide in amounts such that the molar ratio of alkali metal hydroxide to the acrylonitrile repeating unit of the graft copolymer is from about 0.1:1 to about 7:1.

After saponification, which forms the water-soluble form of the polymerized composition, the pH of the saponification solution is generally adjusted to between 6.5 and 7.5 by adding a suitable acid. The copolymer is then isolated by slowly adding an alcohol during agitation until a colloidal precipitate forms. Upon the appearance of the colloidal precipitate, a slight excess of alcohol (i.e., about 10 percent excess) is added to ensure complete precipitation of the copolymer. The alcohol is then removed from the copolymer. An additional amount of fresh alcohol equal in volume to that previously used in added to the precipitated copolymer. This alcohol may be added rapidly, as the slow addition process is only necessary during the initial precipitation step. The mixture is then stirred with the alcohol for 2 to 5 minutes. This alcohol is then removed and a third equal portion of alcohol is added. The mixture is again stirred for 2 to 5 additional minutes.

At this point the alcohol is removed from the copolymer in a manner which provides minimal exposure to and preferably absence of contact with water or moisture-laden air in order to maximize the proportion of the polymer which exhibits properties of a soft gel. Copolymer particles which come into contact with water at this point will coalesce and a hard gel of lower absorbency will result. Therefore the overall absorbency of the produced copolymer particles will be reduced depending upon the amount of water which is allowed to come into contact with the copolymer during the drying step.

After the alcohol is removed, the copolymer is preferably immediately dried at a suitable temperature, such as, for example, about 180° F. to 200° F. After drying, the copolymer may be exposed to ambient air without detrimental effects to the desired soft gel properties.

The alcohol is initially added at a rate such that it is taken up by the polymerized composition without showing an excess thereof within the solution. The solution should be stirred or agitated by suitable means during the addition of the alcohol to provide uniform distribution of the alcohol within the solution during the precipitation step. The alcohol may be added incrementally or as a continuous stream, and the solution to which the alcohol is added need not be maintained within any specific temperature range in order to provide for the formation of the colloidal precipitate.

The amount of alcohol required to provide for the complete precipitation of a specific amount of the polymer composition will generally be relatively constant. That is, the amount of alcohol (based on the weight of the alcohol) which is added to completely precipitate the polymer is from about 8 to about 30, preferably from about 10 to about 16, times the weight of the polymer in solution. However, upon determination of the amount of alcohol required to provide for complete precipitation of a specified amount of the composition, the required amount of alcohol cannot then be added substantially at one time since a large singular mass of the composition will then be formed. Such a mass differs significantly from the fine colloidal particles of the composition which is formed by the alcohol addition method of the present invention. Thus the alcohol must be added at a rate such that the take up of the alcohol by the composition in solution is optimized without any excess thereof accumulating within the solution, which rate is generally from about 2 to about 10, preferably from about 3 to about 6, milliliters of alcohol per gram of polymer per minute.

Any alcohol which is capable of causing the colloidal precipitation of the graft copolymer upon slow addition to the saponification reaction mixture may be used. Generally, however, alcohols selected from the group consisting of methanol, ethanol, propanol and mixtures thereof are preferred for use in the process of the present invention.

The product which is produced by the present invention has a water absorbency of above 3000 and up to about 10,000 parts of water per part of the copolymer composition based on the weight of each. The absorbency is measured by adding 100 milligrams of the copolymer to a graduate, adding 1000 milliliters of water, stirring the mixture and allowing it to stand for 2 hours. The absorbency of the gel is determined by measuring the amount of unabsorbed water from the top of the resulting gel to the 1000 milliliter mark on the graduate and subtracting that amount from the original 1000 milliliters. The absorbency is that amount of water present in the gel multiplied by ten to provide a measure of absorbency in grams of water per gram of copolymer. The product is further characterized in that the copolymer composition, when in the water-absorbent state, is in the form of a soft gel, i.e., a gel which is fluid. As a simple illustration of the characteristics of a soft gel, the copolymer composition of the present invention, upon absorption of water within a beaker, will form a fluid gel which will run out of the beaker when the beaker is turned over. The gel will assume a two-dimensional form when placed upon a flat surface, and no discrete particles of the copolymer composition can be observed within the gel.

The present invention is additionally illustrated in connection with the following Example, which is to be considered illustrative of the present invention but should not be considered limiting thereto.

EXAMPLE 1

A 1000 milliliter flask is charged with 25 grams of yellow corn flour and 420 milliliters of distilled water. The mixture is stirred slowly and heated for 15 minutes at 180° F. to effect gelatinization. The gelatinized dispersion is cooled to 100° F. and 38 grams of acrylonitrile are added and mixed into the dispersion. A solution of 0.85 grams of ceric ammonium nitrate dissolved in 7 milliliters of 1 N nitric acid is then added. The mixture is held under nitrogen for 2 hours and brought to a pH of 7 with a solution of sodium hydroxide. An additional 300 milliliters of distilled water are then mixed into the mixture, and the mixture is heated to a temperature of 180° F. and held at that temperature for 15 minutes to drive off excess acrylonitrile. Then 25 grams of sodium hydroxide dissolved in 50 milliliters of water are mixed into the graft slurry and the temperature is raised to 190° F. The slurry is stirred intermittently until it becomes viscous enough to preclude settling. The temperature is maintained at 190° F. for the duration of the saponification step. A light yellow color is obtained after about 2 hours, indicating that the saponification step is completed.

After saponification, the pH of the slurry is adjusted to between 6.5 and 7.5 by adding acetic acid. The copolymer is then isolated by the slow addition of one liter of absolute methanol. Two additional alcohol washes are conducted using sufficient alcohol to ensure nearly complete removal of water from the slurry. After the third alcohol wash the material is immediately transferred to a Buchner funnel where it is vacuum filtered to remove as much alcohol as possible.

The Buchner funnel is covered with flexible latex during the filtering process to minimize contact with moist air. The copolymer is then immediately transferred to a hot air oven where it is dried at a temperature of 190° F.

One hundred milligrams of the dried polymer are placed in a graduate together with 1,000 milliliters of water and the mixture is then stirred. After 2 hours the amount of water which is not absorbed is determined by observing the level of the top of the gel layer within the graduate. The absorbency of the polymer in this case is 8000 milliliters of water per gram of polymer.

When a similar polymer is made and separated with methanol added quickly and in amounts greater than used herein (as is typical in prior alcohol separation techniques), the resulting polymer forms discrete gel particles upon hydration and has substantially reduced absorbency (i.e., about 2000 times or less its weight in water).

COMPARATIVE EXAMPLE

The differing characteristics of the soft gel produced in Example 1 and a typical hard gel produced under the previously discussed prior art processes may be illustrated as follows.

One hundred milligrams of the dry, ground hard gel polymer are placed in a beaker containing 500 milliliters of distilled water. One hundred milligrams of the dry, ground soft gel polymer of this invention are also placed in a beaker containing 500 milliliters of distilled water. Both polymers are allowed to hydrate for 2 hours.

A sand filter is prepared using a container 3.2 inches in diameter, 2.2 inches in depth, with an 80 mesh sieve on the bottom. One hundred seventy five grams of lake sand are added to the container and spread evenly therein.

One hundred milliliters of the hard gel slurry are poured onto the sand. It takes only 35 seconds for the slurry level to reach the top of the sand layer and for 50 milliliters of the slurry to be collected below the filter.

One hundred milliliters of the soft gel slurry are also poured onto an identical sand filter. It takes about 5 minutes for the first drop of the slurry to appear below the sand. After 90 minutes only 41.5 milliliters of slurry liquid are collected below the filter.

While the invention has been described in connection with a preferred embodiment therof, it is to be understood that the present disclosure is illustrative rather than restrictive and further modifications may be resorted to without departing from the spirit of the invention or the scope of the claims.

We claim:

1. In a method of forming a water-insoluble, aqueous fluid-absorbing copolymer composition wherein acrylonitrile is graft copolymerized onto a starch or corn flour-containing substrate to form a graft copolymer, the graft copolymer saponified to form a water-soluble saponified graft copolymer, isolating and drying said saponified graft copolymer to form a water-insoluble, aqueous fluid-absorbing copolymer composition, the improvement comprising isolating the saponified graft copolymer from solution by alcohol precipitation whereby an alcohol is added to an aqueous solution of said saponified graft copolymer at a rate sufficient to form a colloidal precipitate of said graft copolymer without any excess of the alcohol accumulating in said solution, whereupon the addition of said alcohol is ceased upon complete formation of said colloidal precipitate and the saponified graft copolymer composition is recovered and dried with minimal exposure to water.

2. A method of forming a water-insoluble, aqueous fluid-absorbing copolymer composition comprising:
   (a) graft copolymerizing acrylonitrile onto a starch or corn flour-containing substrate to form a graft copolymer;
   (b) saponifying the graft copolymer in an aqueous solution to form a water-soluble saponified graft copolymer;
   (c) adding an alcohol to said saponified graft copolymer-containing aqueous solution at a rate sufficient to form a colloidal precipitate of said saponified graft copolymer without any excess of the alcohol accumulating in said solution;
   (d) ceasing the addition of said alcohol to said aqueous solution upon complete formation of said colloidal precipitate; and
   (e) recovering and drying said saponified graft copolymer with minimal exposure to moisture to form a water-insoluble, aqueous fluid-absorbing copolymer composition.

3. The method of claim 2 wherein said starch or corn flour-containing substrate is gelatinized prior to the graft copolymerization step.

4. The method of claim 2 wherein the weight ratio of said substrate to acrylonitrile in the graft copolymer is from about 3:1 to about 1:3.

5. The method of claim 2 wherein the graft copolymer is saponified with an alkali metal hydroxide in amounts such that the molar ratio of alkali metal hydroxide to the acrylonitrile repeating unit of the graft copolymer is from about 0.1:1 to about 7:1.

6. The method of claim 2 wherein said alcohol is selected from the group consisting of methanol, ethanol, propanol and mixtures thereof.

7. The process of claim 2 wherein said alcohol is added at a rate of from about 2 to about 10 milliliters of alcohol per gram of copolymer per minute.

8. The process of claim 7 wherein said alcohol is added at a rate of from about 3 to about 6 milliliters of alcohol per gram of copolymer per minute.

9. The product of the process of claim 2.

10. Aqueous fluid-absorbing compositions produced by the process of claim 2 and comprising water-insoluble, alkali salts of saponified graft copolymers of acrylonitrile and a starch or corn flour-containing substrate, said graft copolymers being water-insoluble solids capable of absorbing above about 3000 and up to about 10,000 parts of water by weight per part of said water-insoluble solids while remaining substantially as a soft gel.

* * * * *